US006420151B1

(12) United States Patent
Eikmanns et al.

(10) Patent No.: US 6,420,151 B1
(45) Date of Patent: *Jul. 16, 2002

(54) NUCLEOTIDE SEQUENCES WHICH CODE FOR THE PCK GENE

(75) Inventors: Bernard Eikmanns, Ulm; Christian Riedel, Neu-Ulm; Hermann Sahm, Julich; Bettina Mockel, Bielefeld, all of (DE)

(73) Assignee: Degussa-Huls AG, Hanau (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/455,777

(22) Filed: Dec. 7, 1999

(30) Foreign Application Priority Data

Oct. 20, 1999 (DE) .......................... 199 50 409

(51) Int. Cl.⁷ ................... C12P 21/06; C12N 15/09; C12N 1/20; C12N 15/00
(52) U.S. Cl. .................... 435/194; 435/69.1; 435/183; 435/252.3; 435/320.1; 536/23.2
(58) Field of Search ................ 435/183, 252.3, 435/69.1, 194, 252.32, 320.1

(56) References Cited

U.S. PATENT DOCUMENTS 5,693,781 A * 12/1997 Zupancic et al. ........... 536/24.1
5,726,299 A * 3/1998 Zupancic et al. ........... 536/24.1

FOREIGN PATENT DOCUMENTS

| EP | 0 358 940 | 3/1990 |
| EP | 1 108 790 | 6/2001 |
| WO | WO 01 00844 | 1/2001 |

OTHER PUBLICATIONS

Kramer et al., "Genetic and physiological approaches for the production of amino acids" *Journal of Biotechnology*45: 1–21 1996.

Eikmanns et al., "A family of Corynebacterium glutamicum/ Escherichia coli shuttle vectors for cloning, controlled gene expression, and promoter probing", *Gene*102: 93–98 1991.

Database EMBL ID No. 556812, Mar. 17, 2000.

Jetten et al., 1993, FEMS Letts, vol. 111:183–188.

* cited by examiner

*Primary Examiner*—Rebecca E. Prouty
*Assistant Examiner*—Manjunath Rao
(74) *Attorney, Agent, or Firm*—Pillsbury Winthrop LLP (57) ABSTRACT

Isolated polynucleotide from coryneform bacteria, comprising a polynucleotide sequence chosen from the group consisting of a) polynucleotide which is identical to the extent of at least 70% to a polynucleotide which codes for a polypeptide which comprises the amino acid sequence of SEQ ID No. 2, b) polynucleotide which is identical to the extent of at least 70% to a polynucleotide which codes for the polypeptide which is expressed by the pck gene contained on vector pK19mobsacBΔpck in the deposited *E.coli* strain DSM 13047, c) polynucleotide which codes for a polypeptide which comprises an amino acid sequence which is identical to the extent of at least 70% to the amino acid sequence of SEQ ID No. 2, d) polynucleotide which is complementary to the polynucleotides of a), b) or c) and e) polynucleotide comprising at least 15 successive bases of the polynucleotide sequence of a), b), c) or d).

8 Claims, 3 Drawing Sheets

SEQUENCE LISTING

```
<160> NUMBER OF SEQ ID NOS: 2

<210> SEQ ID NO 1
<211> LENGTH: 3935
<212> TYPE: DNA
<213> ORGANISM: Corynebacterium glutamicum
<220> FEATURE:
<221> NAME/KEY: CDS
<222> LOCATION: (2022)..(3851)

<400> SEQUENCE: 1
ctggcagttc tcctaattga tcgcgggaat tatcagaaat agacattatt tgttattttt      60
cctgttcaac tttaaaactt caatattcgt gagtttggat gaatccctag agcactacct     120
tttagacctc tcgctgcaat ttaggccagt tgagatttaa gctttccgac gattcttctc     180
attactgcaa tcgtaccggc gatggtggac acgatgacat gaaagagcat taaagcaatc     240
aagtacaggc tgaagtagtt aaaccactcc actccggtgc tctgtgataa aaaatgcgca     300
cccaaactca aagtgccaac tgggaaggta ctggcccacc atgtggggct gtatgtcgcc     360
cctttgaaaa cagctctgta gaacacaaag tgagcgatgc ctcccagagg aatcgtaaaa     420
attcccatga tgatgccgta aataatgccc attgtgattg ctgtcttgga tccaaaggac     480
gcaccgatga gctgagctgc tgcagtggat tggcccacca tacccaaagg aatccatgat     540
gttggtgttg ccatcagtgg gatgccctgc gccttgggc cgaaatagta gaaatacact      600
cgggtaaaaa ctgctggtgc agacgccaaa gttaaaagga gagcccgaa agaaacccac      660 agcatcgccg gaagttcaaa gtgctcatgg agttgtgctg ccgaggtgga agcaaccatc     720
ggcgtgacaa gaggaagacc ccacgcaaaa gttggtgtgc ccgccttaga tcgcaaaatg     780
gccgttatat ataaggaata ggcaacaagt cccacggctg tgccaataga ccagcacaca     840
aacataaatc cccacagatc atcacccaaa actacggggc ttgcagttcc caatgcgatc     900
```

-continued

```
aaacccatgg acagcattgc ccatgccggc atgacttcag ttttgaatga aggagagcgg      960
tagattagcc aaccgccaat aatgacaatt gccaccacaa cagctaacgc gaagaagaaa     1020
tctgcgacga ctggaaaacc atggattttc aacagtgatg acaacaatga gatgcccatg    1080
agggaaccag cccacgaggg gccaggtgga ggtaagaccg cagcgtagct tttggtcgaa    1140
gaaggagtgg gcatgcccat tactttaagc ctttgggca gtgaaaccgc taaatgggag    1200
cgttgtgcgc tcgatcactg gtctagacct ttgggctcca aaagttgcaa tttcgcgaat    1260
acttcaacac ttgtttgcaa tgtttgttaa taaatgggtt cgctagtgga ttctgtcgtt    1320
agtactggcc gtcgtggtgg ggtcatgtat ttaggtaggg caaagttaag atcagagcac    1380
tttttgatac gactaactgg atataacctt tggggtaacg tggggatgtg tgtgagtaat    1440
tttcaaagta tttaaaaggg ggatctaggg taaaaatttg gcttcaagta catatcttta    1500
gttcggtagt tgagggcggg tggtgacagt gcgggcatgc atgtgagtgt aaatgttgtt    1560
ttaaaaaggt gtgtactgac agtgggccgg tttgtgctgg tcggccacta gcggagtgct    1620
tggattgtga tggcagggta agggaaaggg attaccatta ccgctgttct tggcgttttg    1680
ttgcctattg tccgaatgtt aagtgttaat ggtgggaaaa ctgggaaagt tgtcccctgg    1740
aatgtgtgag aattgcccaa atctgaaccc aatggccatg gacggggaat gaactgtcgg    1800
agaacggttg aggttaattc ttgaaaccac ccccaaaata ggctatttaa acgggtgctc    1860
tcatattaaa gaaagtgtgt agatgcgtgt gggcagggg taggtccact ggtaatgaca    1920
aatgtgtccg ttgtctcacc taaagtttta actagttctg tatctgaaag ctacgctagg    1980
gggcgagaac tctgtcgaat gacacaaaat ctggagaagt a atg act act gct gca    2036
                                             Met Thr Thr Ala Ala
                                               1               5 atc agg ggc ctt cag ggc gag gcg ccg acc aag aat aag gaa ctg ctg       2084
Ile Arg Gly Leu Gln Gly Glu Ala Pro Thr Lys Asn Lys Glu Leu Leu
            10                  15                  20 aac tgg atc gca gac gcc gtc gag ctc ttc cag cct gag gct gtt gtg       2132
Asn Trp Ile Ala Asp Ala Val Glu Leu Phe Gln Pro Glu Ala Val Val
        25                  30                  35 ttc gtt gat gga tcc cag gct gag tgg gat cgc atg gcg gag gat ctt       2180
Phe Val Asp Gly Ser Gln Ala Glu Trp Asp Arg Met Ala Glu Asp Leu
    40                  45                  50 gtt gaa gcc ggt acc ctc atc aag ctc aac gag gaa aag cgt ccg aac       2228
Val Glu Ala Gly Thr Leu Ile Lys Leu Asn Glu Glu Lys Arg Pro Asn
55                  60                  65 agc tac cta gct cgt tcc aac cca tct gac gtt gcg cgc gtt gag tcc       2276
Ser Tyr Leu Ala Arg Ser Asn Pro Ser Asp Val Ala Arg Val Glu Ser
70                  75                  80                  85 cgc acc ttc atc tgc tcc gag aag gaa gaa gat gct ggc cca acc aac       2324
Arg Thr Phe Ile Cys Ser Glu Lys Glu Glu Asp Ala Gly Pro Thr Asn
            90                  95                  100 aac tgg gct cca cca cag gca atg aag gac gaa atg tcc aag cat tac       2372
Asn Trp Ala Pro Pro Gln Ala Met Lys Asp Glu Met Ser Lys His Tyr
        105                 110                 115 gct ggt tcc atg aag ggg cgc acc atg tac gtc gtg cct ttc tgc atg       2420
Ala Gly Ser Met Lys Gly Arg Thr Met Tyr Val Val Pro Phe Cys Met
    120                 125                 130 ggt cca atc agc gat ccg gac cct aag ctt ggt gtg cag ctc act gac       2468
Gly Pro Ile Ser Asp Pro Asp Pro Lys Leu Gly Val Gln Leu Thr Asp
135                 140                 145 tcc gag tac gtt gtc atg tcc atg cgc atc atg acc cgc atg ggt att       2516
Ser Glu Tyr Val Val Met Ser Met Arg Ile Met Thr Arg Met Gly Ile
```

```
             150                 155                 160                 165
      gaa gcg ctg gac aag atc ggc gcg aac ggc agc ttc gtc agg tgc ctc                2564
      Glu Ala Leu Asp Lys Ile Gly Ala Asn Gly Ser Phe Val Arg Cys Leu
                      170                 175                 180 cac tcc gtt ggt gct cct ttg gag cca ggc cag gaa gac gtt gca tgg                2612
      His Ser Val Gly Ala Pro Leu Glu Pro Gly Gln Glu Asp Val Ala Trp
                      185                 190                 195 cct tgc aac gac acc aag tac atc acc cag ttc cca gag acc aag gaa                2660
      Pro Cys Asn Asp Thr Lys Tyr Ile Thr Gln Phe Pro Glu Thr Lys Glu
                      200                 205                 210 att tgg tcc tac ggt tcc ggc tac ggc gga aac gca atc ctg gca aag                2708
      Ile Trp Ser Tyr Gly Ser Gly Tyr Gly Gly Asn Ala Ile Leu Ala Lys
                      215                 220                 225 aag tgc tac gca ctg cgt atc gca tct gtc atg gct cgc gaa gaa gga                2756
      Lys Cys Tyr Ala Leu Arg Ile Ala Ser Val Met Ala Arg Glu Glu Gly
      230                 235                 240                 245 tgg atg gct gag cac atg ctc atc ctg aag ctg atc aac cca gag ggc                2804
      Trp Met Ala Glu His Met Leu Ile Leu Lys Leu Ile Asn Pro Glu Gly
                      250                 255                 260 aag gcg tac cac atc gca gca gca ttc cca tct gct tgt ggc aag acc                2852
      Lys Ala Tyr His Ile Ala Ala Ala Phe Pro Ser Ala Cys Gly Lys Thr
                      265                 270                 275 aac ctc gcc atg atc act cca acc atc cca ggc tgg acc gct cag gtt                2900
      Asn Leu Ala Met Ile Thr Pro Thr Ile Pro Gly Trp Thr Ala Gln Val
                      280                 285                 290 gtt ggc gac gac atc gct tgg ctg aag ctg cgc gag gac ggc ctc tac                2948
      Val Gly Asp Asp Ile Ala Trp Leu Lys Leu Arg Glu Asp Gly Leu Tyr
      295                 300                 305 gca gtt aac cca gaa aat ggt ttc ttc ggt gtt gct cca ggc acc aac                2996
      Ala Val Asn Pro Glu Asn Gly Phe Phe Gly Val Ala Pro Gly Thr Asn
      310                 315                 320                 325 tac gca tcc aac cca atc gcg atg aag acc atg gaa cca ggc aac acc                3044
      Tyr Ala Ser Asn Pro Ile Ala Met Lys Thr Met Glu Pro Gly Asn Thr
                      330                 335                 340 ctg ttc acc aac gtg gca ctc acc gac gac ggc gac atc tgg tgg gaa                3092
      Leu Phe Thr Asn Val Ala Leu Thr Asp Asp Gly Asp Ile Trp Trp Glu
                      345                 350                 355 ggc atg gac ggc gac gcc cca gct cac ctc att gac tgg atg ggc aac                3140
      Gly Met Asp Gly Asp Ala Pro Ala His Leu Ile Asp Trp Met Gly Asn
                      360                 365                 370 gac tgg acc cca gag tcc gac gaa aac gct gct cac cct aac tcc cgt                3188
      Asp Trp Thr Pro Glu Ser Asp Glu Asn Ala Ala His Pro Asn Ser Arg
                      375                 380                 385 tac tgc gta gca atc gac cag tcc cca gca gca gca cct gag ttc aac                3236
      Tyr Cys Val Ala Ile Asp Gln Ser Pro Ala Ala Ala Pro Glu Phe Asn
      390                 395                 400                 405 gac tgg gaa ggc gtc aag atc gac gca atc ctc ttc ggt gga cgt cgc                3284
      Asp Trp Glu Gly Val Lys Ile Asp Ala Ile Leu Phe Gly Gly Arg Arg
                      410                 415                 420 gca gac acc gtc cca ctg gtt acc cag acc tac gac tgg gag cac ggc                3332
      Ala Asp Thr Val Pro Leu Val Thr Gln Thr Tyr Asp Trp Glu His Gly
                      425                 430                 435 acc atg gtt ggt gca ctg ctc gca tcc ggt cag acc gca gct tcc gca                3380
      Thr Met Val Gly Ala Leu Leu Ala Ser Gly Gln Thr Ala Ala Ser Ala
                      440                 445                 450 gaa gca aag gtc ggc aca ctc cgc cac gac cca atg gca atg ctc cca                3428
      Glu Ala Lys Val Gly Thr Leu Arg His Asp Pro Met Ala Met Leu Pro
                      455                 460                 465 ttc att ggc tac aac gct ggt gaa tac ctg cag aac tgg att gac atg                3476
```

| | |
|---|---|
| Phe Ile Gly Tyr Asn Ala Gly Glu Tyr Leu Gln Asn Trp Ile Asp Met<br>470                        475                      480                     485 | |
| ggt aac aag ggt ggc gac aag atg cca tcc atc ttc ctg gtc aac tgg<br>Gly Asn Lys Gly Gly Asp Lys Met Pro Ser Ile Phe Leu Val Asn Trp<br>                        490                      495                     500 | 3524 |
| ttc cgc cgt ggc gaa gat gga cgc ttc ctg tgg cct ggc ttc ggc gac<br>Phe Arg Arg Gly Glu Asp Gly Arg Phe Leu Trp Pro Gly Phe Gly Asp<br>             505                      510                     515 | 3572 |
| aac tct cgc gtt ctg aag tgg gtc atc gac cgc atc gaa ggc cac gtt<br>Asn Ser Arg Val Leu Lys Trp Val Ile Asp Arg Ile Glu Gly His Val<br>            520                      525                     530 | 3620 |
| ggc gca gac gag acc gtt gtt gga cac acc gct aag gcc gaa gac ctc<br>Gly Ala Asp Glu Thr Val Val Gly His Thr Ala Lys Ala Glu Asp Leu<br>535                        540                      545 | 3668 |
| gac ctc gac ggc ctc gac acc cca att gag gat gtc aag gaa gca ctg<br>Asp Leu Asp Gly Leu Asp Thr Pro Ile Glu Asp Val Lys Glu Ala Leu<br>550                        555                     560                     565 | 3716 |
| acc gct cct gca gag cag tgg gca aac gac gtt gaa gac aac gcc gag<br>Thr Ala Pro Ala Glu Gln Trp Ala Asn Asp Val Glu Asp Asn Ala Glu<br>                        570                      575                     580 | 3764 |
| tac ctc act ttc ctc gga cca cgt gtt cct gca gag gtt cac agc cag<br>Tyr Leu Thr Phe Leu Gly Pro Arg Val Pro Ala Glu Val His Ser Gln<br>            585                      590                     595 | 3812 |
| ttc gat gct ctg aag gcc cgc att tca gca gct cac gct taaagttcac<br>Phe Asp Ala Leu Lys Ala Arg Ile Ser Ala Ala His Ala<br>            600                      605                     610 | 3861 |
| gcttaagaac tgctaaataa caagaaaggc tcccaccgaa agtgggagcc tttcttgtcg | 3921 |
| ttaagcgatg aatt | 3935 |

<210> SEQ ID NO 2
<211> LENGTH: 610
<212> TYPE: PRT
<213> ORGANISM: Corynebacterium glutamicum

<400> SEQUENCE: 2

Met Thr Thr Ala Ala Ile Arg Gly Leu Gln Gly Glu Ala Pro Thr Lys
1               5                   10                  15

Asn Lys Glu Leu Leu Asn Trp Ile Ala Asp Ala Val Glu Leu Phe Gln
            20                  25                  30

Pro Glu Ala Val Val Phe Val Asp Gly Ser Gln Ala Glu Trp Asp Arg
        35                  40                  45

Met Ala Glu Asp Leu Val Glu Ala Gly Thr Leu Ile Lys Leu Asn Glu
    50                  55                  60

Glu Lys Arg Pro Asn Ser Tyr Leu Ala Arg Ser Asn Pro Ser Asp Val
65                  70                  75                  80

Ala Arg Val Glu Ser Arg Thr Phe Ile Cys Ser Glu Lys Glu Asp
            85                  90                  95

Ala Gly Pro Thr Asn Asn Trp Ala Pro Pro Gln Ala Met Lys Asp Glu
        100                 105                 110

Met Ser Lys His Tyr Ala Gly Ser Met Lys Gly Arg Thr Met Tyr Val
    115                 120                 125

Val Pro Phe Cys Met Gly Pro Ile Ser Asp Pro Asp Pro Lys Leu Gly
    130                 135                 140

Val Gln Leu Thr Asp Ser Glu Tyr Val Val Met Ser Met Arg Ile Met
145                 150                 155                 160

Thr Arg Met Gly Ile Glu Ala Leu Asp Lys Ile Gly Ala Asn Gly Ser
            165                 170                 175

```
Phe Val Arg Cys Leu His Ser Val Gly Ala Pro Leu Glu Pro Gly Gln
            180                 185                 190

Glu Asp Val Ala Trp Pro Cys Asn Asp Thr Lys Tyr Ile Thr Gln Phe
            195                 200                 205

Pro Glu Thr Lys Glu Ile Trp Ser Tyr Gly Ser Gly Tyr Gly Gly Asn
            210                 215                 220

Ala Ile Leu Ala Lys Lys Cys Tyr Ala Leu Arg Ile Ala Ser Val Met
225                 230                 235                 240

Ala Arg Glu Glu Gly Trp Met Ala Glu His Met Leu Ile Leu Lys Leu
            245                 250                 255

Ile Asn Pro Glu Gly Lys Ala Tyr His Ile Ala Ala Phe Pro Ser
            260                 265                 270

Ala Cys Gly Lys Thr Asn Leu Ala Met Ile Thr Pro Thr Ile Pro Gly
            275                 280                 285

Trp Thr Ala Gln Val Val Gly Asp Asp Ile Ala Trp Leu Lys Leu Arg
            290                 295                 300

Glu Asp Gly Leu Tyr Ala Val Asn Pro Glu Asn Gly Phe Phe Gly Val
305                 310                 315                 320

Ala Pro Gly Thr Asn Tyr Ala Ser Asn Pro Ile Ala Met Lys Thr Met
            325                 330                 335

Glu Pro Gly Asn Thr Leu Phe Thr Asn Val Ala Leu Thr Asp Asp Gly
            340                 345                 350

Asp Ile Trp Trp Glu Gly Met Asp Gly Asp Ala Pro Ala His Leu Ile
            355                 360                 365

Asp Trp Met Gly Asn Asp Trp Thr Pro Glu Ser Asp Glu Asn Ala Ala
            370                 375                 380

His Pro Asn Ser Arg Tyr Cys Val Ala Ile Asp Gln Ser Pro Ala Ala
385                 390                 395                 400

Ala Pro Glu Phe Asn Asp Trp Glu Gly Val Lys Ile Asp Ala Ile Leu
            405                 410                 415

Phe Gly Gly Arg Arg Ala Asp Thr Val Pro Leu Val Thr Gln Thr Tyr
            420                 425                 430

Asp Trp Glu His Gly Thr Met Val Gly Ala Leu Leu Ala Ser Gly Gln
            435                 440                 445

Thr Ala Ala Ser Ala Glu Ala Lys Val Gly Thr Leu Arg His Asp Pro
450                 455                 460

Met Ala Met Leu Pro Phe Ile Gly Tyr Asn Ala Gly Glu Tyr Leu Gln
465                 470                 475                 480

Asn Trp Ile Asp Met Gly Asn Lys Gly Gly Asp Lys Met Pro Ser Ile
            485                 490                 495

Phe Leu Val Asn Trp Phe Arg Arg Gly Glu Asp Gly Arg Phe Leu Trp
            500                 505                 510

Pro Gly Phe Gly Asp Asn Ser Arg Val Leu Lys Trp Val Ile Asp Arg
            515                 520                 525

Ile Glu Gly His Val Gly Ala Asp Glu Thr Val Val Gly His Thr Ala
            530                 535                 540

Lys Ala Glu Asp Leu Asp Leu Asp Gly Leu Asp Thr Pro Ile Glu Asp
545                 550                 555                 560

Val Lys Glu Ala Leu Thr Ala Pro Ala Glu Gln Trp Ala Asn Asp Val
            565                 570                 575

Glu Asp Asn Ala Glu Tyr Leu Thr Phe Leu Gly Pro Arg Val Pro Ala
            580                 585                 590
```

-continued

```
Glu Val His Ser Gln Phe Asp Ala Leu Lys Ala Arg Ile Ser Ala Ala
        595                 600                 605
His Ala
    610
```

NUCLEOTIDE SEQUENCES WHICH CODE FOR THE PCK GENE

CROSS REFERENCE TO RELATED APPLICATIONS

The present application is based on German application DE 199 50 409.1, filed on Oct. 20, 1999, which disclosure is incorporated herein by reference.

BACKGROUND OF THE INVENTION

1. Field of the Invention

The invention provides nucleotide sequences from coryneform bacteria which code for the pck gene and a process for the fermentative preparation of L-amino acids, in particular L-lysine and L-threonine, by attenuation of the pck gene.

2. Prior Art

Amino acids, in particular lysine and threonine, are used in animal nutrition, in the foodstuffs industry, in the pharmaceuticals industry and in human medicine.

It is known that these substances are prepared by fermentation of strains of coryneform bacteria, in particular Corynebacterium glutamicum. Because of its great importance, work is constantly being undertaken to improve the preparation processes. Improvements to the processes can relate to fermentation measures, such as e.g. stirring and supply of oxygen, or the composition of the nutrient media, such as e.g. the sugar concentration during the fermentation, or the working up to the product form by e.g. ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolism products of regulatory importance and produce the desired amino acid are obtained in this manner.

Methods of the recombinant DNA technique have also been employed for some years for improving the strain of Corynebacterium strains which produce L-amino acid [sic].

OBJECT OF THE INVENTION

The inventors had the object of providing the general public with new measures for improved fermentative preparation of amino acids.

DESCRIPTION OF THE INVENTION

Amino acids, in particular L-lysine and L-threonine, are used in animal nutrition, in the foodstuffs industry, in the pharmaceuticals industry and in human medicine. There is therefore a general interest in providing new improved processes for the preparation of these products.

The invention provides an isolated polynucleotide from coryneform bacteria, comprising a polynucleotide sequence chosen from the group consisting of a) polynucleotide which is identical to the extent of at least 70% to a polynucleotide which codes for a polypeptide which comprises the amino acid sequence of SEQ ID No. 2, b) polynucleotide which is identical to the extent of at least 70% to a polynucleotide which codes for the polypeptide mentioned and is contained on the plasmid pEK-pckA (FIG. 1) or pEK-pckB (FIG. 2), c) polynucleotide which codes for a polypeptide which comprises an amino acid sequence which is identical to the extent of at least 70% to the amino acid sequence of SEQ ID No. 2, d) polynucleotide which is complementary to the polynucleotides of a), b) or c), and e) polynucleotide comprising at least 15 successive bases of the polynucleotide sequence of a), b), c) or d).

The invention also provides a preferably recombinant DNA with Corynebacterium origin which is capable of replication in coryneform microorganisms and contains at least the nucleotide sequence which codes for the pck gene, shown in SEQ ID No. 1.

The invention also provides a DNA according to claim 1 which is capable of replication, comprising (i) the nucleotide sequence shown in SEQ ID no. 1, or (ii) at least one sequence which corresponds to sequence (i) within the range of the degeneration of the genetic code, or (iii) at least one sequence which hybridizes with the sequence complementary to sequence (i) or (ii), and/or optionally (iv) sense mutations of neutral function in (i).

Figure 1:
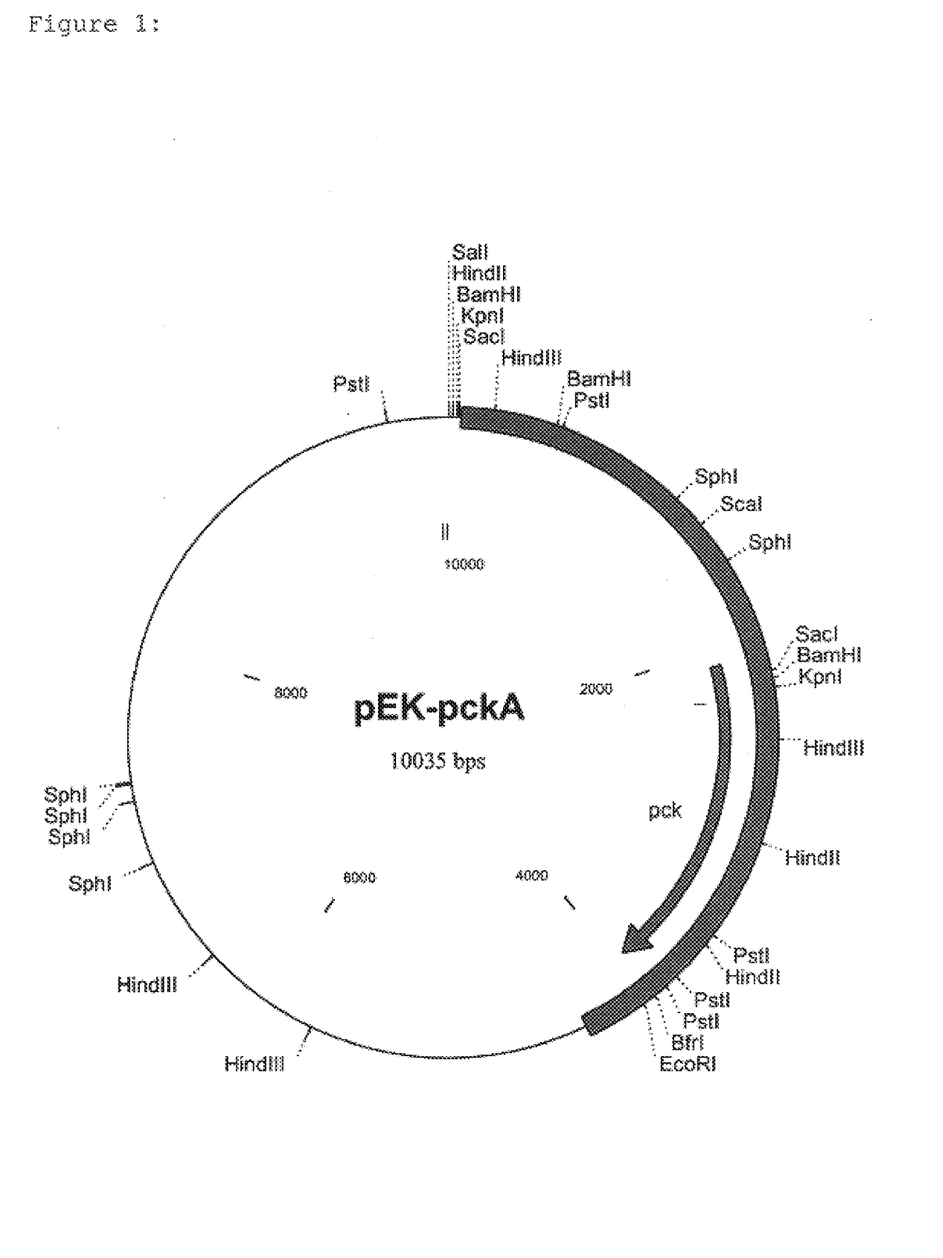
FIG. 1: Restriction map of the plasmid pEK-pckA
Figure 2:
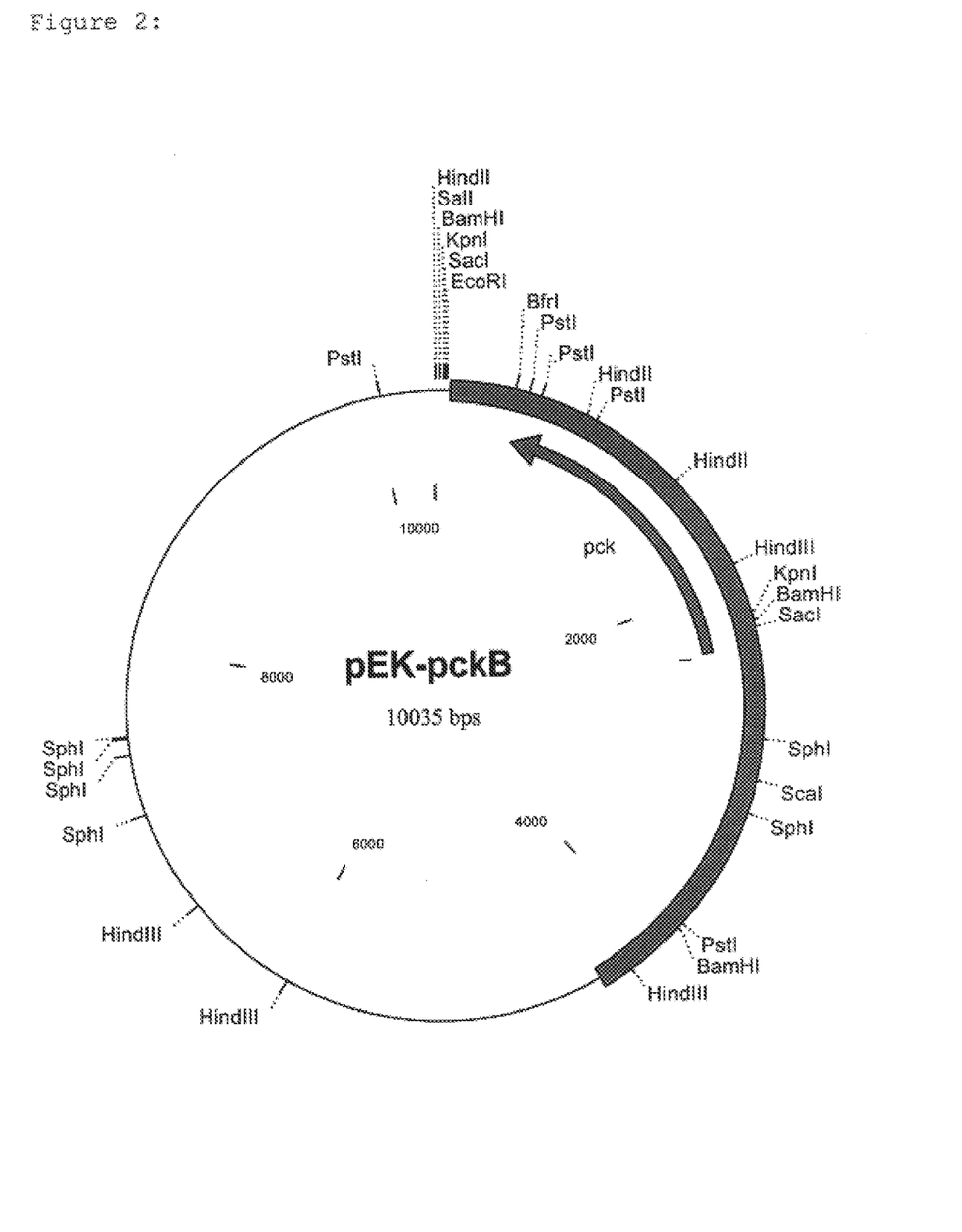
FIG. 2: Restriction map of the plasmid pEK-pckB

The invention also provides a polynucleotide according to claim 2, comprising the nucleotide sequence as shown in SEQ ID no. 1, a polynucleotide according to claim 2, which codes for a polypeptide which comprises the amino acid sequence as shown in SEQ ID No. 2, a vector containing the polynucleotide according to claim 1, in particular pEK-pckA or pEK-pckB, shown in FIGS. 1 and 2 and coryneform bacteria serving as the host cell, into which the Δpck deletion has been incorporated.

The invention also provides polynucleotides which substantially comprise a polynucleotide sequence, which are obtainable by screening by means of hybridization of a corresponding gene library, which comprise the complete gene with the polynucleotide sequence corresponding to SEQ ID no. 1, with a probe which comprises the sequence of the polynucleotide mentioned, according to SEQ ID no. 1 or a fragment thereof, and isolation of the DNA sequence mentioned.

Polynucleotide sequences according to the invention are suitable as hybridization probes for RNA, cDNA and DNA, in order to isolate, in the full length, cDNA which code for phosphoenol pyruvate carboxykinase and to isolate those cDNA or genes which have a high similarity of sequence with that of the phosphoenol pyruvate carboxykinase gene.

Polynucleotide sequences according to the invention are furthermore suitable as primers for the preparation of DNA of genes which code for phosphoenol pyruvate carboxykinase by the polymerase chain reaction (PCR).

Such oligonucleotides which serve as probes or primers comprise at least 30, preferably at least 20, especially preferably at lease 15 successive bases. Oligonucleotides which have a length of at least 40 or 50 base pairs are also suitable.

"Isolated" means separated out of its natural environment.

"Polynucleotide" in general relates to polyribonucleotides and polydeoxyribonucleotides, it being possible for these to be non-modified RNA and DNA or modified RNA and DNA.

"Polypeptides" is understood as meaning peptides or proteins which obtain [sic] two or more amino acids bonded via peptide bonds.

The polypeptides according to the invention include the polypeptide according to SEQ ID No. 2, in particular those with the biological activity of PEP carboxykinase, and also those which are identical to the extent of at least 70% to the polypeptide according to SEQ ID No. 2, preferably to the extent of at least 80%, and in particular those which are identical to the extent of at least 90% to 95% to the polypeptide according to SEQ ID no. 2, and have the activity mentioned.

The invention also provides a process for the fermentative preparation of L-amino acids, in particular L-lysine and L-threonine, using coryneform bacteria which in particular already produce the L-amino acids and in which the nucleotide sequence(s) which code(s) for the pck gene are attenuated, in particular expressed at a low level.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding enzyme (protein), and optionally combining these measures.

The microorganisms which the present invention provides can produce L-amino acids, in particular lysine and threonine, from glucose, sucrose, lactose, fructose, maltose, molasses, starch, cellulose or from glycerol and ethanol. They can be representatives of coryneform bacteria, in particular of the genus Corynebacterium. Of the genus Corynebacterium, there may be mentioned in particular the species *Corynebacterium glutamicum*, which is known among specialists for its ability to produce L-amino acids.

Suitable strains of the genus Corynebacterium, in particular of the species *Corynebacterium glutamicum*, are, for example, the known wild-type strains

*Corynebacterium glutamicum* ATCC13032

*Corynebacterium acetoglutamicum* ATCC15806

*Corynebacterium acetoacidophilum* ATCC13870

*Corynebacterium thermoaminogenes* FERM BP-1539

*Corynebacterium melassecola* ATCC17965

*Brevibacterium flavum* ATCC14067

*Brevibacterium lactofermentum* ATCC13869 and

*Brevibacterium divaricatum* ATCC14020 and L-amino acid-producing mutants or strains prepared therefrom, such as, for example, the lysine-producing strains

*Corynebacterium glutamicum* FERM-P 1709

*Brevibacterium flavum* FERM-P 1708

*Brevibacterium lactofermentum* FERM-P 1712

*Corynebacterium glutamicum* FERM-P 6463

*Corynebacterium glutamicum* FERM-P 6464 and

*Corynebacterium glutamicum* DSM5714 or such as, for example, the L-threonine-producing strains

*Corynebacterium glutamicum* ATCC21649

*Brevibacterium flavum* BB69

*Brevibacterium flavum* DSM5399

*Brevibacterium lactofermentum* FERM-BP 269

*Brevibacterium lactofermentum* TBB-10

*Corynebacterium glutamicum* MH20-22B-DR17.

The inventors have succeeded in isolating the new pck gene of *C. glutamicum* which codes for the enzyme phosphoenol pyruvate carboxykinase (PEP carboxykinase) (EC 4.1.1.49).

To isolate the pck gene or also other genes of *C. glutamicum*, a gene library of this microorganism is first set up in *E. coli*. The setting up of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990) or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 set up in λ vectors by Kohara et al. (Cell 50, 495–508 (1987)). Bathe et al. (Molecular and General Genetics, 252:255–265, 1996) describe a gene library of *C. glutamicum* ATCC13032, which was set up with the aid of the cosmid vector SuperCos I (Wahl et al., 1987, Proceedings of the National Academy of Sciences USA, 84:2160–2164) in the *E.coli* K-12 strain NM554 (Raleigh et al., 1988, Nucleic Acids Research 16:1563–1575). Börmann et al. (Molecular Microbiology 6(3), 317–326)) in turn describe a gene library of *C. glutamicum* ATCC13032 using the cosmid pHC79 (Hohn and Collins, Gene 11, 291–298 (1980)).

To prepare a gene library of *C. glutamicum* in *E. coli*, it is also possible to use plasmids or plasmid vectors, such as, for example, pBR322 (Bolivar, Life Sciences, 25, 807–818 (1979)), pUC9 (Vieira et al., 1982, Gene, 19:259–268), pACYC177 (Chang and Cohen, Journal of Bacteriology 134, 1141–1156 (1978)) or pSC101 (Cohen and Chang, Journal of Bacteriology 132, 734–737 (1977)). Suitable hosts are, in particular, those *E. coli* strains which are restriction- and recombination-defective.

The gene library is then incorporated into an indicator strain by transformation (Hanahan, Journal of Molecular Biology 166, 557–580, 1983) or electroporation (Tauch et.al., 1994, FEMS Microbiological Letters, 123:343–347). The indicator strain is distinguished in that it has a mutation in the gene of interest which causes a detectable phenotype. In the context of the present invention, the *E. coli* mutant HG4 described by Goldie and Sanwal (Journal of Bacteriology 141: 1115–1121 (1980)) is of importance. This strain carried a mutation in the pck gene, as a result of which growth on succinate as the sole source of carbon is severely impaired. By transformation with a vector which contains the pck gene, growth on succinate can be re-established.

The long DNA fragments cloned with the aid of cosmids or other vectors can than be subcloned into known plasmid vectors in the form of shorter DNA fragments. Assignment of the gene according to the invention to a specific DNA section is made possible as a result. For this, plasmid vectors known from the prior art, such as e.g. pBR322 (Bolivar, Life Sciences, 25, 807–818 (1979)) or the pSU vectors described by Bartolomé et al. (Gene 102, 75–78 (1991)) are used. However, shuttle vectors which replicate both in *Escherichia coli* and in *Corynebacterium glutamicum*, such as e.g. pZ1 (Menkel et al., Applied and Environmental Microbiology (1989) 64: 549–554) or pEK0 (Eikmanns et al., Gene 102 (1991)) are preferably used, so that investigations can be carried out in both species. Examples of these are the plasmids pEK-pckA (FIG. 1) and pEK-pckB (FIG. 2), which were prepared starting from the plasmid vector pEK0 and carry the pck gene according to the invention.

The DNA sections characterized in this manner are then again subcloned into the usual vectors suitable for DNA sequencing. Alternatively, the long DNA sections cloned in cosmids can be subcloned directly into sequencing vectors. Examples of such vectors which are suitable for DNA sequencing are the plasmids pGEM-5zf(−) or pGEM-5zf(+) from the company Promega Corporation (Promega Protocols and Application Guide, Second Edition, 1991, part number Y981, Promega Corporation, Madison, Wis., USA).

Methods of DNA sequencing are described, inter alia, by Sanger et al. (Proceedings of the National of Sciences of the United States of America USA, 74:5463–5467, 1977).

The DNA sequences obtained can then be investigated with known algorithms or sequence analysis programs, such as e.g. that of Staden (Nucleic Acids Research 14, 217–232 (1986)), the GCG program of Butler (Methods of Biochemical Analysis 39, 74–97 (1998)) the FASTA algorithm of Pearson and Lipman (Proceedings of the National Academy of Sciences USA 85,2444–2448 (1988)) or the BLAST algorithm of Altschul et al. (Nature Genetics 6, 119–129 (1994)) and compared with the sequence entries which exist in databanks accessible to the public. Databanks for nucleotide sequences which are accessible to the public are, for example, that of the European Molecular Biologies Laboratories (EMBL, Heidelberg, Germany) of that of the National Center for Biotechnology Information (NCBI, Bethesda, Md., USA).

The new DNA sequence of *C. glutamicum* which codes for the pck gene and which, as SEQ ID No. 1, is a constituent of the present invention was obtained in this manner. The amino acid sequence of the corresponding protein has furthermore been derived from the present DNA sequence by the methods described above. The resulting amino acid sequence of the pck gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID no. 1 are a constituent of the invention. Such oligonucleotides typically have a length of at least 15 base pairs.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al. (International Journal of Systematic Bacteriology (1991) 41: 255–260). Instructions for amplification of DNA sequences with the aid of the polymerase chain reaction (PCR) can be found by the expert, inter alia, in the handbook by Gait: Oligonukleotide [sic] synthesis: a practical approach (IRL Press, Oxford, UK, 1984) and in Newton and Graham: PCR (Spektrum Akademischer Verlag, Heidelberg, Germany, 1994).

The inventors have found that coryneform bacteria produce L-amino acids, in particular lysine and threonine, in an improved manner after attenuation of the pck gene.

To achieve an attenuation, either the expression of the pck gene or the catalytic properties of the enzyme protein can be reduced or eliminated. The two measures can optionally be combined.

The reduction in gene expression can take place by suitable culturing or by genetic modification (mutation) of the signal structures of gene expression. Signal structures of gene expression are, for example, repressor genes, activator genes, operators, promoters, attenuators, ribosome binding sites, the start codon and terminators. The expert can find information on this e.g. in the patent application WO 96/15246, in Boyd and Murphy (Journal of Bacteriology 170: 5949 (1988)), in Voskuil and Chambliss (Nucleic Acids Research 26: 3548 (1998)), in Jensen and Hammer (Biotechnology and Bioengineering 58: 191 (1998)), in Patek et al. (Microbiology 142: 1297 (1996) and in known textbooks of genetics and molecular biology, such as e.g. the textbook by Knippers ("Molekulare Genetik [Molecular Genetics]", 6th edition, Georg Thieme Verlag, Stuttgart, Germany, 1995) or that by Winnacker ("Gene und Klone [Genes and Clones]", VCH Verlagsgesellschaft, Weinheim, Germany, 1990).

Mutations which lead to a change or reduction in the catalytic properties of enzyme proteins are known from the prior art; examples which may be mentioned are the works by Qiu and Goodman (Journal of Biological Chemistry 272: 8611–8617 (1997)), Sugimoto et al. (Bioscience Biotechnology and Biochemistry 61: 1760–1762 (1997)) and M öckel ("Die Threonindehydratase aus *Corynebacterium glutamicum*: Aufhebung der allosterischen Regulation und Struktur des Enzyms [Threonine dehydratase from *Corynebacterium glutamicum*: Cancelling the allosteric regulation and structure of the enzyme]", Reports from the Julich Research Centre, Jül-2906, ISSN09442952, Jülich, Germany, 1994). Comprehensive description can be found in known textbooks of genetics and molecular biology, such as e.g. that by Hagemann ("Allgemeine Genetik [General Genetics]", Gustav Fischer Verlag, Stuttgart, 1986).

Possible mutations are transitions, transversions, insertions and deletions. Depending on the effect of the amino acid exchange on the enzyme activity, missense mutations or nonsense mutations are referred to. Insertions or deletions of at least one base pair in a gene lead to frame shift mutations, which lead to incorrect amino acids being incorporated or translation being interrupted prematurely. Deletions of several codons typically lead to a complete loss of the enzyme activity. Instructions on generation of such mutations are prior art and can be found in known textbooks of genetics and molecular biology, such as e.g. the textbook by Knippers ("Molekulare Genetik [Molecular Genetics]", 6th edition, Georg Thieme Verlag, Stuttgart, Germany, 1995), that by Winnacker ("Gene und Klone [Genes and Clones]", VCH Verlagsgesellschaft, Weinheim, Germany, 1990) or that by Hagemann ("Allgemeine Genetik [General Genetics]", Gustav Fischer Verlag, Stuttgart, 1986).

Figure 3:
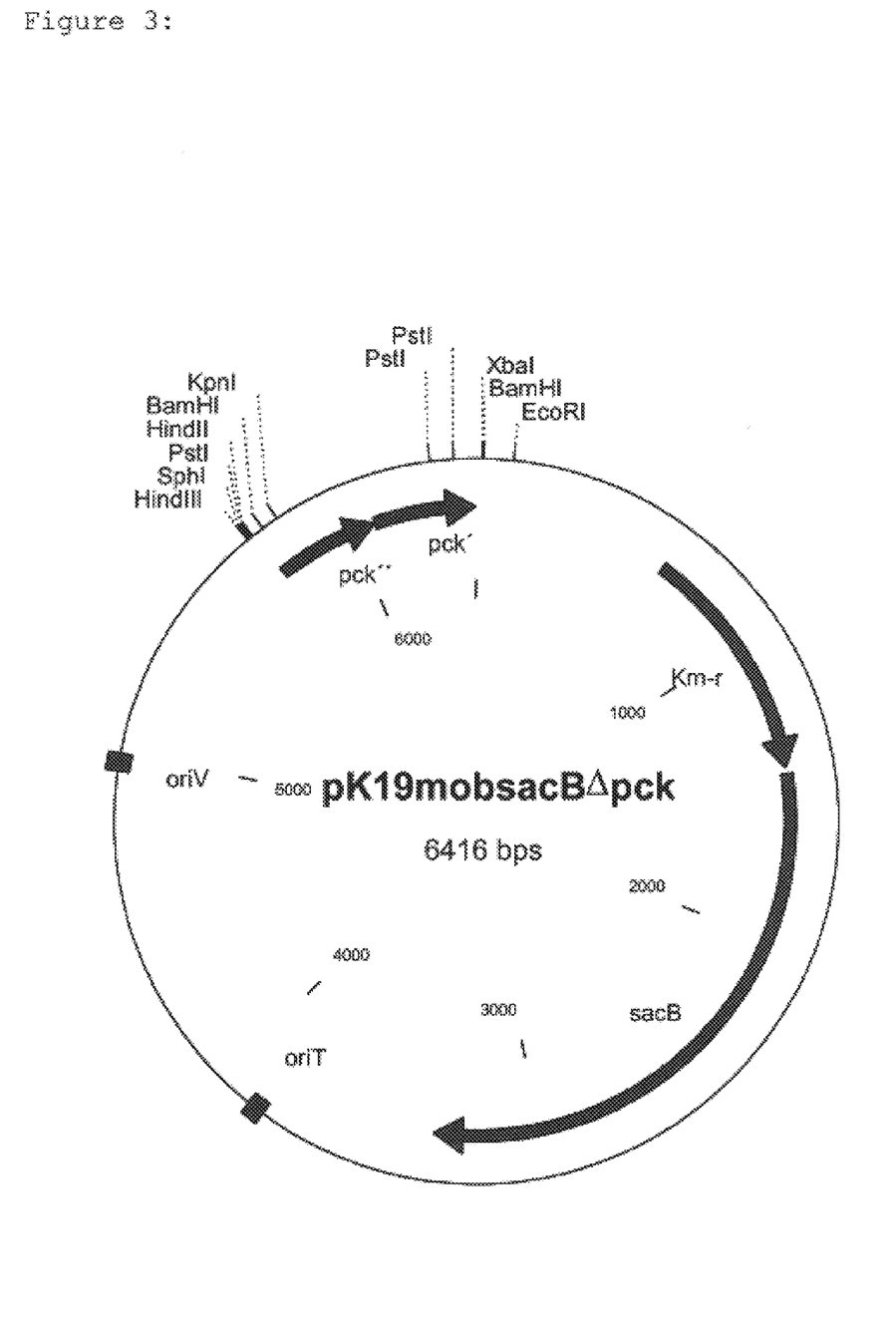
FIG. 3: Restriction map of the plasmid pk19mobsacBΔpck

An example of a mutated pck gene is the Δpck allele contained in the plasmid pK19mobsacBΔpck (FIG. 3). The Δpck allele contains only the 5' and the 3' flanks of the pck gene; a section of the coding region 1071 bp long is missing (deletion). This Δpck allele can be incorporated into coryneform bacteria by integration mutagenesis. The abovementioned plasmid pK19mobsacBΔpck, which is not capable of replication in *C. glutamicum*, is used for this. After transfer by conjugation or transformation and homologous recombination by means of a first "cross-over" event which effects integration and a second "cross-over" event which effects excision in the pck gene, the incorporation of the Δpck allele is achieved and a total loss of the enzyme function in the particular strain is achieved.

Instructions and explanations on integration mutagenesis are to be found, for example, in Schwarzer and Pühler (Bio/Technology 9,84–87 (1991)) or Peters-Wendisch et al. (Microbiology 144, 915–927 (1998)).

Examples of amino acid-producing strains of coryneforme bacteria with an attenuated pck gene are the lysine-producing strain MH20-22BΔpck and the threonine-producing strain DM368-2Δpck.

In addition, it may be advantageous for the production of L-amino acids to over-express one or more enzymes of the particular biosynthesis route, in addition to attenuation of the pck gene.

Thus, for example, for the preparation of L-lysine
at the same time the dapA gene which codes for dihydrodipicolinate synthase can be over-expressed (EP-B 0 197 335), or at the same time a DNA fragment which imparts S-(2-aminoethyl)-cysteine resistance can be amplified (EP-A 0 088 166).

Thus, for example, for the preparation of L-threonine at the same time the hom gene which codes for homoserine dehydrogenase (Peoples et al., Molecular Microbiology 2, 63–72 (1988)) or the $hom^{dr}$ or $hom_{FBR}$ allele which codes for a "feed back resistant" homoserine dehydrogenase (Archer et al., Gene 107, 53–59 (1991); Reinscheid et al., Journal of Bacteriology 173, 3228–3230 (1991)) can be over-expressed.

In addition to attenuation of the pck gene it may furthermore be advantageous, for the production of L-amino acids, in particular lysine and threonine, to eliminate undesirable side reactions (Nakayama: "Breeding of Amino Acid Producing Micro-organisms", in: Overproduction of Microbial Products, Krumphanzl, Sikyta, Vanek (eds.), Academic Press, London, UK, 1982).

The microorganisms prepared according to the invention can be cultured continuously or discontinuously in the batch process (batch culture) or in the fed batch (feed process) or repeated fed batch process (repetitive feed process) for the purpose of production of L-amino acids, in particular L-lysine and L-threonine. A summary of known culture methods are [sic] described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981). Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substances can be used individually or as a mixture. Organic nitrogen-containing compounds, such as peptones, yeast extract, meat extract, malt extract, corn steep liquor, soya bean flour and urea, or inorganic compounds, such as ammonium sulphate, ammonium chloride, ammonium phosphate, ammonium carbonate and ammonium nitrate, can be used as the source of nitrogen. The sources of nitrogen can be used individually or as a mixture. Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during culturing in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH. Antifoams, such as e.g. fatty acid polyglycol esters, can be employed to control the development of foam. Suitable substances having a selective action, e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of the desired L-amino acid has formed. This target is usually reached within 10 hours to 160 hours.

The following microorganism has been deposited at the Deutsche Sammlung für Mikrorganismen und Zellkulturen (DSMZ=German Collection of Microorganisms and Cell Cultures, Braunschweig, Germany) in accordance with the Budapest Treaty:

Escherichia coli strain DH5α/pK19mobsacBΔpck as DSM 13047

The process according to the invention is used for the fermentative preparation of L-amino acids, in particular L-aspartic acid, L-asparagine, L-homoserine, L-threonine, L-isoleucine and L-methionine, with coryneform bacteria, in particular the preparation of L-lysine and L-threonine.

EXAMPLES

The present invention is explained in more detail in the following with the aid of embodiment examples.

For this purpose, inter alia, experiments were carried out with the lysine producer Corynebacterium glutamicum strain MH20-22B and the threonine producer Brevibacterium flavum strain DM368-2. Strain MH20-22B has been deposited as DSM5715 (EP-B-0435 132) and strain DM368-2 as DSM5399 EP-B-0385 940) at the Deutsche Sammlung für Mikroorganismen und Zellkulturen (DSMZ, Braunschweig, Germany) in accordance with the Budapest Treaty.

Example 1

Isolation of the pck Gene

To isolate the PEP carboxykinase gene (pck) from C. glutamicum a cosmid gene library was set up on the basis of the cosmid pHC79 (Hohn and Collins, Gene 11 (1980) 291–298) by a known method (Sambrook et al., Molecular Cloning, A Laboratory Handbook, 1989, Cold Spring Harbour Laboratory Press). For this, chromosomal DNA was isolated from C. glutamicum ATCC13032 (Eikmanns et al., Microbiology 140 (1994) 1817–1828) and partly digested with the restriction enzyme Sau3A. After ligation of the resulting fragments into the BamHI cleavage site of the cosmid pHC79, the batch was packed into the protein envelope of the lambda bacteriophage and the E. coli strain ED8654 (Murray et al. Molecular and General Genetics 150 (1997) 53–61) was transfected with this. The recombinant cosmids were packed into the protein envelope of the lambda phage by a method of Sternberg et al. (Gene 1 (1979) 255–280), and the transfection of E. coli ED8654 was carried out by a method of Sambrook et al. (Molecular Cloning, A Laboratory Handbook, 1989, Cold Spring Harbour Laboratory Press). The corresponding cosmids were isolated from a total of 30 resulting recombinant E. coli clones (Sambrock et al., Molecular Cloning, A Laboratory Handbook, 1989, Cold Spring Harbour Laboratory Press) and subjected to a restriction analysis with the enzyme HindIII. It was found that 24 of the cosmids possessed inserts, and that the inserts had sizes of approximately 35 kb. A total of 2200 cosmid-carrying E. coli clones were combined, and the cosmid DNA was prepared from this mixture by known processes (Sambrock et al., Molecular Cloning, A Laboratory Handbook, 1989, Cold Spring Harbour Laboratory Press).

To isolate the pck gene from *C. glutamicum*, the cosmide gene library was transformed into the PEP carboxykinase-defective *E. coli* mutant HG4 (Goldie and Sanwal, Journal of Bacteriology 141 (1980) 115–1121) by known processes (Sambrock et al., Molecular Cloning, A Laboratory Handbook, 1989, Cold Spring Harbour Laboratory Press). Because it is PEP carboxykinase-defective, the mutant HG4 is no longer capable of growing on succinate as the only source of carbon. After transformation of the cosmid gene library into this mutant, a total of 1200 clones were obtained. Of these, a total of two clones showed growth on M9 minimal medium (Sambrock et al., Molecular Cloning, A Laboratory Handbook, 1989, Cold Spring Harbour Laboratory Press) with succinate (0.4%) as the only source of carbon. After isolation of the corresponding cosmids (Sambrock et al., Molecular Cloning, A Laboratory Handbook, 1989, Cold Spring Harbour Laboratory Press) from these clones and renewed transformation into the *E. coli* mutant HG4, the resulting clones were again capable of growing on M9 medium with succinate as the only source of carbon.

To limit the pck gene from *C. glutamicum* to a smaller fragment, the two complementing cosmids were digested with the restriction enzymes XhoI, ScaI and PvuII and separated in an electrical field on a 0.8% agarose gel by known methods (Sambrock et al., Molecular Cloning, A Laboratory Handbook, 1989, Cold Spring Harbour Laboratory Press). Fragments in the size range above 3.0 kb were isolated from the gel by electroelution (Sambrock et al., Molecular Cloning, A Laboratory Handbook, 1989, Cold Spring Harbour Laboratory Press) and ligated into the SalI (XhoI-digestion) or into the Klenow-treated EcoRI cleavage site (ScaI and PvuII digestion) of the vector pEK0 (Eikmanns et al., Gene 102 (1991) 93–98). *E. coli* HG4 was transformed with the ligation batches and the resulting transformants were investigated again for their ability to grow on succinate as the sole source of carbon. Seven clones with plasmids which allowed growth of the mutant HG4 on succinate were found in the transformation batch with the PvuII ligation batch. The corresponding plasmids were isolated from the recombinant strains and subjected to restriction mapping. It was found that all seven plasmids carried the same 4.3 kb PvuII insert, three in one orientation and four in the other. The newly constructed plasmids were called pEK-pckA and pEK-pckB, depending on the orientation of the insert in the vector. The restriction maps of the two plasmids are shown in FIG. 1 and 2.

Example 2
Sequencing of the pck Structural Gene and Adjacent Regions

For the sequencing, the approximately 3.9 kb EcoRI fragment was isolated from pEK-pckA (an EcoRI cleavage site here originates from the vector pEK0) by known methods. The overhanging ends of the fragment were filled up to blunt ends with Klenow polymerase (Sambrock et al., Molecular Cloning, A Laboratory Handbook, 1989, Cold Spring Harbour Laboratory Press) and ligated into the EcoRV cleavage site of the vector pGEM-5Zf(+)(Promega Corporation, Madison, Wis., USA). The insertion of the plasmid thus generated was sequenced by the chain-stopping sequencing method (Sanger et al., Proceedings of the National Academy of Sciences USA, 74 (1977) 5463–5467). It is shown as SEQ IN no. 1. The resulting nucleotide sequence of 3935 bp was analysed with the HUSAR program package (release 3.0) of the Deutsche Krebsforschungszentrum (DKFZ=German Cancer Research Centre, Heidelberg, Germany). The sequence analysis of the fragments showed an open reading frame of 1830 bp in length, which codes for a protein consisting of 610 amino acids.

Example 3
Over-expression of the pck Gene

The plasmids pEK-pckA and pEK-pckB were introduced into the *C. glutamicum* strain ATCC13032 by electroporation with subsequent selection on kanamycin(50 µg/ml)-containing BHI agar plates (Liebl et al., FEMS Microbiology Letters 65 (1989) 299–304) and the resulting strains were called ATCC13032/pEK-pckA and ATCC13032/pEK-pckB. These two strains and the starting strain were cultured in Luria-Bertani complex medium [Sambrook et al., Molecular Cloning, A laboratory manual (1989) Cold Spring Harbour Laboratory Press] and the PEP carboxykinase test was carried out in accordance with the method described by Bentle and Lardy [Journal of Biological Chemistry 251 (1976) 2916–2921]. The result of the analysis is shown in table 1, and shows that the PEP carboxykinase activity in the two strains with the plasmids pEK-pckA and pEK-pckB is 10 to 12 times higher than in the starting strain.

TABLE 1

PEP carboxykinase activity in various strains

| Strain | PEP carboxykinase (nmol min$^{-1}$ mg protein$^{-1}$) |
|---|---|
| ATCC13032 | 120 |
| ATCC13032/pEK-pckA | 1270 |
| ATCC13032/pEK-pckB | 1510 |

Example 4
Preparation of an Integration Plasmid for Deletion Mutagenesis of the pck Gene For inactivation of the PEP carboxykinase gene, the EcoRI-SacI fragment of the pck gene was isolated from the vector pEK-pckB (FIG. 2) and ligated into the vector pGEM-7Zf(+) (Promega Corporation, Madison, Wis., USA). A pck-internal 1.07 kb HindII-HindIII fragment was deleted from the resulting plasmid, and the pck gene with the 1.07 kb deletion was then isolated as the BfrI-SacI frament and, after the overhanging ends had been filled up, was ligated into the vector pk19mobsacB, which is non-replicative in *C. glutamicum* (Schäfer et al., Gene 145, 69–73 (1994)). In the integration plasmid pK19mobsacBΔpck (FIG. 3) constructed in this way, the 5' region of the pck gene (350 bp) is directly adjacent to the 3' region of the pck gene (340 bp); in the genome, the two regions are separated from one another by 1071 bp. Up to this step, all clonings were carried out in *E. coli* DH5α as the host.

Example 5
Deletion mutagenesis of the pck Gene in the Lysine Producer MH20-22B

*E. coli* S17-1 was then transformed with the integration plasmid pK19mobsacBΔpck (Simon et al., Bio/Technology 1,784–791 (1983)). This strain allows transfer of a plasmid to *Corynebacterium glutamicum* by conjugation (Schäfer et al., Journal of Bacteriology 172 (1990) 1663–1666). The lysine production strain *C. glutamicum* MH20-22B was used as the recipient of the conjugation (Schrumpf et al., Applied Microbiology and Biotechnology 37 (1992) 566–571)). Several transconjugants were obtained from the conjugation between *E. coli* S17-1/pk19mobsacBΔpck and *C. glutamicum* MH20-22B and subsequent selection on Luria-Bertani agar plates with kanamycin (25 μg/ml) and nalidixic acid (50 μg/ml). For selection for the second recombination event, which is to lead to excision of the vector together with the pck gene, these transconjugants were cultured on antibiotic-free Luria-Bertani complex medium [Sambrook et al; Molecular Cloning, A laboratory manual (1989) Cold Spring Harbour Laboratory Press] with 1% glucose and then plated out on the same medium plus 10% sucrose. The sacB gene present on the vector pk19mobsacB codes for the enzyme levan sucrase and leads to synthesis of levan from sucrose. Since levan is toxic to *C. glutamicum*, only *C. glutamicum* cells which have lost the integration plasmid can grow on sucrose-containing medium (Jäger et al., Journal of Bacteriology 174 (1992) 5462–5466). 30 sucrose-resistant clones were investigated for their kanamycin sensitivity. For 11 of the clones tested, in addition to the sucrose resistance, the desired kanamycin sensitivity could also be confirmed. In these 11 clones, the vector background had therefore been excised again. Whether the desired deletion had also taken place was tested by analysis by means of the polymerase chain reaction (PCR). For this, chromosomal DNA was liberated from a colony of the starting strain and from colonies of the 11 kanamycin-sensitive clones. For this, the particular colony was removed from the agar plate with a toothpick, suspended in 50 μl $H_2O$ and incubated for 5 minutes at 95° C. 1 μl portions of the resulting solution were each employed as templates in the PCR. Oligonucleotides which cover the regions from nucleotide 2136 to 2158 and from 3815 to 3793 in SEQ ID No. 1 were used as primers. The PCR conditions were: prior denaturing: 150 seconds at 94° C.; denaturing 60 seconds at 94° C.; hybridization 30 seconds at 60° C.; amplification 120 seconds at 72° C.; 30 cycles, end extension 240 seconds at 72° C. On the basis of the primers chosen, a PCR product of 1.68 kb was expected in the batch with the DNA of the starting strain. A PCR product of 0.61 kb was expected in the PCR with the pck deletion mutant. A PCR product 0.61 kb in size was obtained with one clone. The desired deletion of the internal 1071 bp pck fragment in this clone was thereby demonstrated. The clone was called MH20-22BΔpck. The 1.68 kb PCR product was detected in the batches of the other clones. In these, the vector had thus been excised such that the genomic starting situation was re-established.

The strain MH20-22BΔpck and the starting strain MH20-22B were grown in Luria-Bertani complex medium plus 1% glucose und the PEP carboxykinase test was carried out in accordance with the method described by Bentle and Lardy (Journal of Biological Chemistry 251 (1976) 2916–2921). The result of the analysis (table 2) shows that PEP carboxykinase activity is no longer detectable in the mutant MH20-22BΔpck, in contrast to the starting strain MH20-22B.

TABLE 2

PEP carboxykinase activity in various strains

| Strain | PEP carboxykinase (nmol min$^{-1}$ mg protein$^{-1}$) |
|---|---|
| MH20-22B | 65 |
| MH20-22BΔpck | <3 * |

* 3 nmol min$^{-1}$ mg protein$^{-1}$ is the detection limit

Example 6
Production of L-lysine

To investigate the effect of the inactivation of the PEP carboxykinase gene on lysine production, the strain MH20-22B (Schrumpf et al., Applied Microbiology and Biotechnology 1992, 37:566–571) and the PEP carboxykinase-negative mutant MH20-22BΔpck (example 5) was [sic] cultured in Luria-Bertani complex medium plus 1% glucose and the fermentation medium CGXII (Keilhauer et al., Journal of Bacteriology 1993, 175:5595–5603) was inoculated from the two pre-cultures (5% inokulum, optical density at 600 nm approximately 0.5). The medium additionally comprised 3 mM leucine, since the two strains are leucine-auxotrophic. The batches each comprise 60 ml culture, obtained in 500 ml conical flasks with baffles. After culture for 24 hours at 28° C. on a rotary shaking machine of the Certomat S/50 type (B. Braun Biotech International, Melsungen, Germany) at 120 rpm, the concentration of the lysine secreted into the medium was determined.

The amino acid concentration was determined by means of high pressure liquid chromatography (Jones und Gilligan, Journal of Chromatography 1983, 266:471–482). The result of the fermentation is shown in table 3.

TABLE 3

Lysine concentration in the culture supernatant of the strains MH20-22B and MH20-22BΔpck

| Strain | L-Lysine (mM) |
|---|---|
| MH20-22B | 54 |
| MH20-22BΔpck | 65 |

Example 7
Deletion Mutagenesis of the pck Gene in the Threonine Producer DM368-2

As in the case of the lysine producer MH20-22B, using the *E. coli* strain S17-1/pk19mobsacBΔpck a conjugation with the threonine producer DM368-2 with subsequent selection for the first and second recombination was carried out (see example 5). Of 30 sucrose-resistant clones, 14 were kanamycin-sensitive. Of these, the 1071 bp deletion in the pck gene could be detected with the aid of the PCR analysis described in example 5 in two clones, called DM368-2Δpck6 and DM368-2Δpck18.

An enzyme test with the starting strain DM368-2 and the two pck deletion strains DM368-2Δpck16 and DM368-2Δpck18, carried out as described in example 5, showed that no PEP carboxykinase activity is detectable in these mutants 5 (Table 4).

TABLE 4

PEP carboxykinase activity in various strains

| Strain | PEP carboxykinase (nmol min$^{-1}$ mg protein$^{-1}$) |
|---|---|
| DM368-2 | 79 |
| DM368-2BΔpck16 | <3 * |
| DM368-2BΔpck18 | <3 * |

* 3 nmol min$^{-1}$ mg protein$^{-1}$ is the detection limit

Example 8
Production of L-threonine

Analogously to the experiments on L-lysine production, the accumulation of threonine in the culture supernatant of the PEP carboxykinase-defective strain DM368-2BΔpck16 was 15 investigated in comparison with the starting strain DM368-2. For this, the two strains were cultured in Luria-Bertani complex medium plus 1% glucose and the fermentation medium CGXII was inoculated from the precultures. After culture for 24 hours at 28° C. on a rotary shaking machine at 120 rpm, the concentration of the threonine secreted into the medium was determined.

The amino acid concentration was determined by means of high pressure liquid chromatography (see above). The result of the fermentation is shown in table 5.

TABLE 5

Threonine concentration in the culture supernatant of the strains DM 368-2 and DN 368-2Δpck16

| Strain | L-Threonine (mM) |
|---|---|
| DM368-2 | 8 |
| DM368-2Δpck16 | 22 |

Figures

The following figures are attached.

The base pair numbers stated are approx. values obtained in the context of reproducibility.

The abbreviations and designations have the following meaning:

| | |
|---|---|
| sacB: | sacB gene |
| ori V: | Replication origin V |
| ori T: | Replication origin for the transfer |
| Km-r: | Kanamycin resistance |
| KpnI: | Cleavage site of the restriction enzyme KpnI |
| HindIII: | Cleavage site of the restriction enzyme HindIII |
| HindII: | Cleavage site of the restriction enzyme HindII |
| PstI: | Cleavage site of the restriction enzyme PstI |
| SphI: | Cleavage site of the restriction enzyme SphI |
| XbaI: | Cleavage site of the restriction enzyme XbaI |
| SalI: | Cleavage site of the restriction enzyme SalI |
| SacI: | Cleavage site of the restriction enzyme SacI |
| BfrI: | Cleavage site of the restriction enzyme BfrI |
| ScaI: | Cleavage site of the restriction enzyme ScaI |
| BamHI: | Cleavage site of the restriction enzyme BamHI |
| EcoRI: | Cleavage site of the restriction enzyme EcoRI |
| pck': | 3' terminal fragment of the pck gene |
| pck": | 5' terminal fragment of the pck gene |
| pck: | pck gene |

What is claimed is:

1. An isolated polynucleotide from coryneform bacteria, comprising a polynucleotide sequence selected from the group consisting of:
   a) a polynucleotide which encodes a polypeptide comprising the amino acid sequence of SEQ ID NO:2;
   b) a polynucleotide which encodes a polypeptide comprising the amino acid sequence of SEQ ID NO:2, and which is contained on the plasmid pEK-pckA (FIG. 1) or pEK-pckB (FIG. 2); and
   c) a polynucleotide which is complementary to the polynucleotides of either a) or b).

2. The isolated polynucleotide of claim 1, wherein said polynucleotide is a DNA which is capable of replication.

3. The isolated polynucleotide of claim 1, wherein said polynucleotide is an RNA.

4. An isolated polynucleotide comprising the nucleic acid sequence of SEQ ID NO:1.

5. The isolated polynucleotide of claim 2 consisting of either:
   (i) the nucleotide sequence of SEQ ID NO:1, or
   (ii) sense mutations of neutral function in (i).

6. The polynucleotide sequence as claimed in claim 2, which codes for a polypeptide which comprises the amino acid sequence shown in SEQ ID NO:2.

7. A vector pk19mobsacBΔpck, shown in FIG. 3 and deposited in the strain E.coli DH5α under number DSM 13047.

8. Coryneform bacteria serving as host cells, wherein said bacteria have been transformed with a vector comprising the isolated polynucleotide of claim 1.

* * * * *